(12) United States Patent
Toyomura et al.

(10) Patent No.: US 6,270,997 B1
(45) Date of Patent: Aug. 7, 2001

(54) DNA ENCODING PORCINE COMPLEMENT INHIBITOR

(75) Inventors: Koji Toyomura; Hiroshi Murakami; Tamotsu Shigehisa, all of Tsukuba (JP)

(73) Assignee: Nippon Meat Packers, Inc., Osaka (JP)

( * ) Notice: Subject to any disclaimer, the term of this patent is extended or adjusted under 35 U.S.C. 154(b) by 0 days.

(21) Appl. No.: 08/981,234

(22) PCT Filed: Jun. 19, 1996

(86) PCT No.: PCT/JP96/01704

§ 371 Date: Apr. 13, 1998

§ 102(e) Date: Apr. 13, 1998

(87) PCT Pub. No.: WO97/00951

PCT Pub. Date: Jan. 9, 1997

(30) Foreign Application Priority Data

Jun. 20, 1995 (JP) .................................................... 7-178254

(51) Int. Cl.⁷ .......................... C07H 21/04; C12N 15/15; C12Q 1/68
(52) U.S. Cl. .............................. 435/69.2; 435/6; 435/455; 536/23.5
(58) Field of Search .............................. 435/6, 69.2, 455; 536/23.5

(56) References Cited

U.S. PATENT DOCUMENTS 5,705,732 * 1/1998 Sims ........................................ 800/2

OTHER PUBLICATIONS

Naeve, C.W. et al., Accuracy of automated DNA sequencing: a multi–laboratory comparison of sequencing results, Biotechniques, 19(3):448–453, 1995.*
Hosokawa et al., *The Journal of Immunology*, vol. 157, pp. 4946–4952 (1996).
Toyomura et al., *International Immunology*, vol. 9, No. 6, pp. 869–876 (1997).
Tsujimura et al., *Biochem. J.*, vol. 330, pp. 163–168 (1998).

* cited by examiner

Primary Examiner—David Saunders
Assistant Examiner—Mary Beth Tung
(74) Attorney, Agent, or Firm—Birch, Stewart, Kolasch & Birch, LLP.

(57) ABSTRACT

This invention is related to the DNA encoding the porcine complement inhibitor (pMCPcDNA), the porcine complement inhibitor expressed by the DNA, and a method for screening for the porcine complement inhibitor. pMCPcDNA can be obtained by preparing a cDNA library from porcine vascular endothelium and screening for cDNA encoding the porcine complement inhibitor. pMCPcDNA of this invention is useful for production of the porcine complement inhibitor by genetic recombination and for analysis for the promoter region of the porcine complement inhibitor.

6 Claims, 1 Drawing Sheet

SEQUENCE LISTING (1) GENERAL INFORMATION:

(iii) NUMBER OF SEQUENCES: 2

(2) INFORMATION FOR SEQ ID NO:1:

-continued

```
     (i) SEQUENCE CHARACTERISTICS:
         (A) LENGTH: 1365 base pairs
         (B) TYPE: nucleic acid
         (C) STRANDEDNESS: double
         (D) TOPOLOGY: linear (ii) MOLECULE TYPE: cDNA to mRNA (ix) FEATURE:
         (A) NAME/KEY: CDS
         (B) LOCATION: 59..1147

(xi) SEQUENCE DESCRIPTION: SEQ ID NO:1:

GGAACTCGGA GAGGTCTCCG CTAGGCTGGT GTCGGGTTAC CTGCTCATCT TCCCGAAA         58

ATG ATG GCG TTT TGC GCG CTG CGC AAG GCA CTT CCC TGC CGT CCC GAG        106
Met Met Ala Phe Cys Ala Leu Arg Lys Ala Leu Pro Cys Arg Pro Glu
 1               5                  10                  15

AAT CCC TTT TCT TCG AGG TGC TTC GTT GAG ATT CTT TGG GTG TCG TTG        154
Asn Pro Phe Ser Ser Arg Cys Phe Val Glu Ile Leu Trp Val Ser Leu
                 20                  25                  30

GCC CTA GTG TTC CTG CTT CCC ATG CCC TCA GAT GCC TGT GAT GAG CCA        202
Ala Leu Val Phe Leu Leu Pro Met Pro Ser Asp Ala Cys Asp Glu Pro
             35                  40                  45

CCG AAG TTT GAA AGC ATG CGG CCC CAA TTT TTG AAT ACC ACT TAC AGA        250
Pro Lys Phe Glu Ser Met Arg Pro Gln Phe Leu Asn Thr Thr Tyr Arg
         50                  55                  60

CCT GGA GAC CGT GTA GAG TAT GAA TGT CGC CCC GGG TTC CAG CCC ATG        298
Pro Gly Asp Arg Val Glu Tyr Glu Cys Arg Pro Gly Phe Gln Pro Met
 65                  70                  75                  80

GTT CCT GCG CTT CCC ACC TTT TCC GTC TGT CAG GAC GAT AAT ACG TGG        346
Val Pro Ala Leu Pro Thr Phe Ser Val Cys Gln Asp Asp Asn Thr Trp
                 85                  90                  95

TCA CCC CTC CAG GAG GCT TGT CGA CGA AAA GCC TGT TCG AAT CTA CCA        394
Ser Pro Leu Gln Glu Ala Cys Arg Arg Lys Ala Cys Ser Asn Leu Pro
                100                 105                 110

GAC CCG TTA AAT GGC CAA GTT AGC TAC CCA AAT GGG GAT ATG CTG TTT        442
Asp Pro Leu Asn Gly Gln Val Ser Tyr Pro Asn Gly Asp Met Leu Phe
            115                 120                 125

GGT TCA AAG GCT CAG TTT ACC TGT AAC ACT GGT TTT TAC ATA ATT GGA        490
Gly Ser Lys Ala Gln Phe Thr Cys Asn Thr Gly Phe Tyr Ile Ile Gly
        130                 135                 140

GCC GAG ACT GTG TAT TGT CAG GTT TCT GGG AAT GTT ATG GCC TGG AGT        538
Ala Glu Thr Val Tyr Cys Gln Val Ser Gly Asn Val Met Ala Trp Ser
145                 150                 155                 160

GAG CCC TCC CCG CTA TGT GAG AAG ATT TTG TGT AAA CCA CCT GGC GAA        586
Glu Pro Ser Pro Leu Cys Glu Lys Ile Leu Cys Lys Pro Pro Gly Glu
                165                 170                 175

ATT CCA AAT GGA AAA TAC ACC AAT AGC CAT AAG GAT GTA TTT GAA TAC        634
Ile Pro Asn Gly Lys Tyr Thr Asn Ser His Lys Asp Val Phe Glu Tyr
            180                 185                 190

AAT GAA GTA GTA ACT TAC AGT TGT CTT TCT TCA ACT GGA CCG GAT GAA        682
Asn Glu Val Val Thr Tyr Ser Cys Leu Ser Ser Thr Gly Pro Asp Glu
        195                 200                 205

TTT TCA CTT GTT GGA GAG AGC AGC CTT TTT TGT ATT GGG AAG GAC GAG        730
Phe Ser Leu Val Gly Glu Ser Ser Leu Phe Cys Ile Gly Lys Asp Glu
    210                 215                 220

TGG AGT AGT GAC CCC CCT GAG TGT AAA GTG GTC AAA TGT CCA TAT CCA        778
Trp Ser Ser Asp Pro Pro Glu Cys Lys Val Val Lys Cys Pro Tyr Pro
225                 230                 235                 240

GTA GTC CCA AAT GGA GAA ATT GTA TCA GGA TTT GGA TCA AAA TTT TAC        826
Val Val Pro Asn Gly Glu Ile Val Ser Gly Phe Gly Ser Lys Phe Tyr
                245                 250                 255
```

-continued

| | |
|---|---|
| TAC AAA GCA GAG GTT GTA TTT AAA TGC AAT GCT GGT TTT ACC CTT CAT<br>Tyr Lys Ala Glu Val Val Phe Lys Cys Asn Ala Gly Phe Thr Leu His<br>              260                    265                    270 | 874 |
| GGC AGA GAC ACA ATT GTC TGC GGT GCA AAC AGC ACG TGG GAG CCT GAG<br>Gly Arg Asp Thr Ile Val Cys Gly Ala Asn Ser Thr Trp Glu Pro Glu<br>            275                    280                    285 | 922 |
| ATG CCC CAA TGT ATC AAA GAT TCC AAG CCT ACT GAT CCA CCT GCA ACC<br>Met Pro Gln Cys Ile Lys Asp Ser Lys Pro Thr Asp Pro Pro Ala Thr<br>290                    295                    300 | 970 |
| CCA GGA CCA AGC CAT CCA GGA CCT CCC AGT CCC AGT GAT GCA TCA CCA<br>Pro Gly Pro Ser His Pro Gly Pro Pro Ser Pro Ser Asp Ala Ser Pro<br>305                  310                    315                    320 | 1018 |
| CCT AAA GAT GCT GAG AGT TTA GAT GGA GGA ATC ATC GCT GCA ATT GTT<br>Pro Lys Asp Ala Glu Ser Leu Asp Gly Gly Ile Ile Ala Ala Ile Val<br>            325                    330                    335 | 1066 |
| GTG GGC GTC TTA GCT GCC ATT GCA GTA ATT GCT GGT GGT GTA TAC TTT<br>Val Gly Val Leu Ala Ala Ile Ala Val Ile Ala Gly Gly Val Tyr Phe<br>            340                    345                    350 | 1114 |
| TTT CAT CAT AAA TAC AAC AAG AAA AGG TCG AAG TAAAACTGAT GTGCTTAAAG<br>Phe His His Lys Tyr Asn Lys Lys Arg Ser Lys<br>            355                    360 | 1167 |
| TAAAAGTTGC TGAGAGGACG TGGAATCCAG CCCCTTCCCT CTCCTGTGCT GCTGCCTGGG | 1227 |
| TCCCGTTTTG CATGTCATGA CTGTGTGCTT CCAAAAAATG CCTTTTGTTC GTATTTTTTT | 1287 |
| GCCTAAACGC ATGATTTTGT CTCTACTTGA ATTAAATCAT CACTGAATCC ACGCAAAAAA | 1347 |
| AAAAAAAAAA AAAAAAA | 1365 |

(2) INFORMATION FOR SEQ ID NO:2:

(i) SEQUENCE CHARACTERISTICS:
        (A) LENGTH: 363 amino acids
        (B) TYPE: amino acid
        (D) TOPOLOGY: linear (ii) MOLECULE TYPE: protein (xi) SEQUENCE DESCRIPTION: SEQ ID NO:2:

Met Met Ala Phe Cys Ala Leu Arg Lys Ala Leu Pro Cys Arg Pro Glu
 1              5                   10                 15

Asn Pro Phe Ser Ser Arg Cys Phe Val Glu Ile Leu Trp Val Ser Leu
              20                   25                 30

Ala Leu Val Phe Leu Leu Pro Met Pro Ser Asp Ala Cys Asp Glu Pro
            35                   40                 45

Pro Lys Phe Glu Ser Met Arg Pro Gln Phe Leu Asn Thr Thr Tyr Arg
  50                   55                   60

Pro Gly Asp Arg Val Glu Tyr Glu Cys Arg Pro Gly Phe Gln Pro Met
65                    70                   75                 80

Val Pro Ala Leu Pro Thr Phe Ser Val Cys Gln Asp Asn Thr Trp
              85                   90                 95

Ser Pro Leu Gln Glu Ala Cys Arg Arg Lys Ala Cys Ser Asn Leu Pro
           100                  105               110

Asp Pro Leu Asn Gly Gln Val Ser Tyr Pro Asn Gly Asp Met Leu Phe
         115                  120               125

Gly Ser Lys Ala Gln Phe Thr Cys Asn Thr Gly Phe Tyr Ile Ile Gly
  130                 135                 140

Ala Glu Thr Val Tyr Cys Gln Val Ser Gly Asn Val Met Ala Trp Ser
145                  150                  155               160

-continued

```
Glu Pro Ser Pro Leu Cys Glu Lys Ile Leu Cys Lys Pro Pro Gly Glu
            165                 170                 175

Ile Pro Asn Gly Lys Tyr Thr Asn Ser His Lys Asp Val Phe Glu Tyr
            180                 185                 190

Asn Glu Val Val Thr Tyr Ser Cys Leu Ser Ser Thr Gly Pro Asp Glu
        195                 200                 205

Phe Ser Leu Val Gly Glu Ser Ser Leu Phe Cys Ile Gly Lys Asp Glu
    210                 215                 220

Trp Ser Ser Asp Pro Pro Glu Cys Lys Val Val Lys Cys Pro Tyr Pro
225                 230                 235                 240

Val Val Pro Asn Gly Glu Ile Val Ser Gly Phe Gly Ser Lys Phe Tyr
            245                 250                 255

Tyr Lys Ala Glu Val Val Phe Lys Cys Asn Ala Gly Phe Thr Leu His
            260                 265                 270

Gly Arg Asp Thr Ile Val Cys Gly Ala Asn Ser Thr Trp Glu Pro Glu
            275                 280                 285

Met Pro Gln Cys Ile Lys Asp Ser Lys Pro Thr Asp Pro Pro Ala Thr
        290                 295                 300

Pro Gly Pro Ser His Pro Gly Pro Pro Ser Pro Ser Asp Ala Ser Pro
305                 310                 315                 320

Pro Lys Asp Ala Glu Ser Leu Asp Gly Gly Ile Ile Ala Ala Ile Val
            325                 330                 335

Val Gly Val Leu Ala Ala Ile Ala Val Ile Ala Gly Gly Val Tyr Phe
            340                 345                 350

Phe His His Lys Tyr Asn Lys Lys Arg Ser Lys
        355                 360
```

DNA ENCODING PORCINE COMPLEMENT INHIBITOR

This application is the national phase under 35 U.S.C. §371 of prior PCT International Application No. PCT/JP 96/01704 which has an International filing date of Jun. 19, 1996 which designated the United States of America, the entire contents of which are hereby incorporated by reference.

FIELD OF THE INVENTION

This invention provides DNA encoding a porcine complement inhibitor. More particularly, the invention provides the DNA encoding an inhibitor protein which inhibits the porcine complement activity, the inhibitor protein expressed by the gene, and a screening method for the complement-inhibitor gene.

BACKGROUND OF THE INVENTION

Recently, organ transplantation has been widely carried out in various countries. Development of highly effective immunosuppressants (Cyclosporin, FK506 and the like) has solved the problems of rejection of organs transplanted from man to man, however, lack of donors has become a serious problem. Such a problem has prompted studies on animal-to-man organ transplantation, namely xenotransplantation. Although approximately 3,500 heart transplantations are being performed annually in European countries and the United States, they cover only approximately 20 to 30% of patients who need heart transplantation. Use of animals closely related to human beings as donors (for example, such primates as baboons, chimpanzees and the like) involves a great deal of difficulty due to shortage of these animals and their high intelligence, but use of domestic animals as donors involves less problems. Particularly, pigs have advantages of easy supply due to mass rearing, their organ sizes similar to those of man, and established basic technology including maintenance of the strains. Consequently, organ transplantation from pigs to man has been studied.

Of rejections occurring in pig-to-man organ transplantation, acute rejection by Major Histocompatibility Complex (MHC)-related cellular immunity may not occur, since evolutional relatedness between pigs and man is so scarce that there is no similarity between their MHCs. Moreover, application of such effective immunosuppressants may avoid such rejection, if ever occurs.

Human blood, however, contains endogenous antibodies against pigs (namely, natural antibodies). Consequently, if a porcine organ is transplanted to man, the natural antibodies recognize the organ (antigen) resulting in formation of antigen-antibody complexes, which activate human complements. The activated human complements cause necrosis of the transplanted organ (rejection). Such a phenomenon occurs immediately (within an hour) after transplantation, so it is termed hyperacute rejection.

No drug inhibiting hyperacute rejection caused by complement activation has ever been developed. No human organ is injured by human complements, since factors preventing complement activation are expressed in human organs. Such factors are named complement inhibitors (or complement-inhibiting factors). Of the complement inhibitors, three factors, DAF (decay accelerating factor, CD55), MCP (membrane cofactor protein, CD46) and CD59, are important. It is believed that DAF and MCP inhibit activation of complements by accelerating the destruction of C3b and C3/C5 convertase, and CD59 does so by inhibiting the C9 step.

The complement inhibitors are species-specific. Porcine complement inhibitors can inhibit the complement activity of pigs but not that of man. The porcine complement inhibitors cannot inhibit human complements activated by the porcine organ transplanted to man. Therefore, the porcine organ transplanted to human undergoes necrosis.

Such problems arising when a porcine organ is transplanted to man will be solved, if human complement inhibitors are expressed in the porcine organs by genetic engineering. In transplantation of the porcine heart, there will be no problem if the human complement inhibitors are being expressed by porcine vascular endotherial cells. From such a viewpoint, studies on recombinant pigs (transgenic pigs) integrated with human complement-inhibitor genes have widely been carried out.

As described above, xenotransplantation by using transgenic pigs integrated with the human complement-inhibitor genes have been studied. Up to the present, promoters derived from the human complement-inhibitor gene and from viruses have been used to prepare such transgenic pigs. For the complement inhibitors to be expressed in pigs, however, the promoters orginating from pigs may be more efficient. To obtain such promoters, cDNA of the porcine complement inhibitors is needed, however, no such cDNA has ever been known.

From these viewpoints, the present inventors conducted cloning for expression of porcine complement-inhibitor cDNA and succeeded in obtaining cDNA which could make the cells resistant against the porcine complement and highly homologous to human MCP. During the course of these studies, the inventors found also a novel method for screening for cDNA libraries.

This invention was accomplished on the basis of such findings. The purposes of the invention were to provide cDNA for the porcine complement inhibitor, the porcine complement-inhibitor protein, and the method for screening for the complement-inhibitor gene.

SUMMARY OF THE INVENTION

This invention relates to the base sequence defined by Sequence No. 1 or DNA comprising a part of its base sequence, particularly DNA comprising or containing the 59th-to-1,147th bases of the DNA sequence defined by Sequence No. 1.

Another invention provides the porcine complement inhibitor comprising the amino-acid sequence defined by Sequence No. 2; the DNA encoding the amino-acid sequence defined by Sequence No. 2 or the DNA comprising the sequence, and the method for screening for the clones possessing the complement-inhibitor genes by introducing a cDNA library to the host cells, adding complements and the antibody against the host, and then separating the surviving hosts.

DESCRIPTION OF THE PREFERRED EMBODIMENTS

Figure 1:
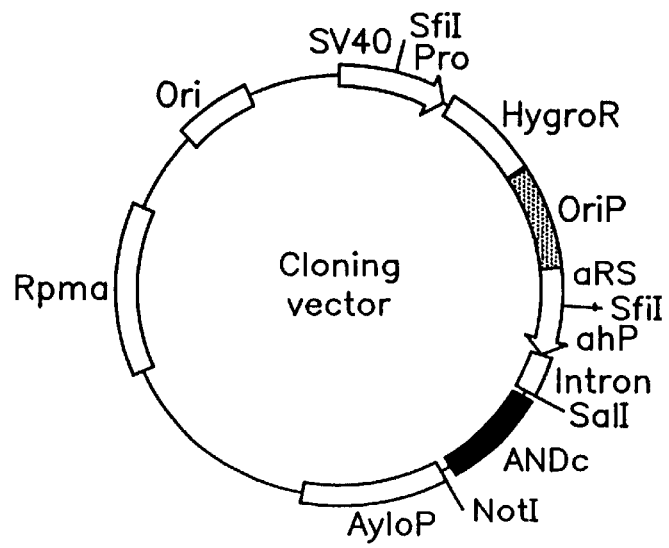
FIG. 1 outlines theplasmid cDNA library.

The base sequence of this invention defined by Sequence No. 1 is cDNA encoding the porcine complement inhibitor (hereinafter referred to as pMCPcDNA), and the cDNA is prepared, for example, by the following methods:

First, mRNA is prepared. mRNA can be prepared by conventional methods. Total RNA can be extracted from the cells, tissues and the like expressing the porcine complement inhibitors by such conventional methods as the guanisium-thiocyanate method, the hot phenol method and the lithium-salt method. Poly(A)$^+$RNA (mRNA) can be prepared by applying the RNA obtained on an oligo (dT)-cellulose column. At this step, porcine vascular endothelial cells, which are considered to be a highly expressing site of the complement inhibitors, are used favorably as a cell source. A primary cell culture of the porcine vascular endothelial cells or established PAE cells are being favorably used (see J. Biol. Chem., 262, 4098, 1987).

Next, cDNA can be conventionally synsthesized from poly(A)$^+$RNA (for example, Gubler et al., Gene, 25, 263, 1983) or a commercially available cDNA-synthesis kit. A cDNA library is prepared by such conventional methods as inserting the obtained cDNA into a phage vector $\lambda$gt11 or into appropriate plasmid vectors after separating long base pairs, if necessary.

pMCPcDNA is cloned from cDNA library thus prepared. Although cloning of pMCPcDNA can conventionally be done by the plaque-hybridization method, colony-hybridization method and the method using specific conjugated antibodies, the novel screening method utilizing the anti-complement activity established by the present inventors is more favorably applied.

Namely, the cells possessing aimed cDNA can be cloned by introduction of the cDNA library into the appropriate cells, activation of the complement by adding both antibody against the cells (anti-serum) and complement components (serum of aimed species; in this case, porcine serum), and selection of the cells possessing anti-complement activities. More particularly, as indicated in the examples described below, the plasmid vector library is introduced into human lymphoblast JY25 cells (see J. Immunology, 141, 4283, 1988), and then the aimed cells are preliminarily selected by the conventional methods. Since an anti-antibiotic gene has been incorporated in the plasmid vector, the vector-introduced cells can survive and proliferate in a medium containing the corresponding antibiotics. Although the cells are preliminarily selected in an antibiotic-containing medium to increase the selectivity, such method can be omitted sometimes.

Then, the complement activity is stimulated by addition of both anti-JY25 antibody (antiserum) and complement components (serum of the aimed species; in this case, the porcine serum) to the preliminarily selected cells. The cells to which the pMCP-gene-containing plasmid has been introduced can survive, since the complement inhibitor is being expressed. By repeating selections with both the antibiotic-containing medium and the complement, the cells containing aimed cDNA (pMCPcDNA) can be cloned.

By this method, cDNA of the porcine complement inhibitors (pMCP and other porcine complement inhibitors) can easily be obtained. Moreover, complement-inhibitor cDNA of various other animals can easily be obtained by applying this method to cDNA libraries of various animal species. pMCPcDNA (or cDNA fragments containing a part of them) can be isolated from the selected clones in accordance with the conventional cDNA-isolation method. If necessary, pMCPcDNA (or its parts) can be isolated by subcloning the cDNA. If DNA is a part of pMCPcDNA, clones possessing the full-length pMCPcDNA will be obtained by screening the cDNA library with the DNA as a probe.

Bases of pMCPcDNA thus obtained can be sequenced by such conventional methods as the dideoxy method or by using a sequence-determination kit commercially available (for example, an Applied-Biosystems' DNA sequencer).

By above-described methods, cloning and sequencing pMCPcDNA were accomplished. pMCPcDNA obtained in the example described below consisted of 1,365 bp (Sequence No. 1). The region encoding the porcine complement inhibitor was 1,089 bp, of which approximately 600-bp translation region was highly homologous (70%) to human MCP cDNA. From the base sequence of Sequence No. 1, the total amino-acid residues of the porcine complement inhibitor (Sequence No. 2) was 363.

pMCPcDNA thus obtained is useful for production of the porcine complement inhibitor, for a sufficient amount of the inhibitor can be produced by conventional genetic engineering with pMCPcDNA. For example, the porcine complement inhibitor can be obtained by cultivating the transformant obtained by introducing the expression vector prepared by incorporating pMCPcDNA into a proper vector, which was then introduced into a proper host. Such a DNA fragment encoding the amino-acid sequence defined by Sequence No. 2 or that containing this DNA fragment may be incorporated into the vector.

Such a vector that comprises a promoter necessary for expression, SD sequence, terminator, enhancer, or various kinds of markers may be used, if necessary. As a host, such bacteria as *Escherichia coli, Bacillus subtilis* and the like, such microorganisms as yeast, or animal or plant cells can be used. It is commonly known by those skilled in the art that the aimed peptide may vary in the saccharide chain or the extent of glycosylation depending upon the host cells used, and that the terminal amino-acid sequence of the peptide obtained is variable due to modification of N and/or C terminal(s) of the precursor peptide expressed in the host cells by processing with a signal peptidase and the like.

The porcine complement inhibitor of this invention, defined by Sequence No.2, inhibiting activation of the porcine and human complements, is useful as a complement-activation inhibitor.

As far as possessing essentially the same effects as those of the porcine complement inhibitor of this invention, defined by Sequence No.2, it will be validated if a part(s) of the amino-acid sequence are deleted or replaced or inserted with other amino acids or the N and/or C terminal(s) are conjugated with one or more amino acids, or sugar chain(s) are deleted or replaced.

As described above, by using pMCPcDNA of this invention, the porcine complement inhibitor can be produced by genetic engineering, and sufficient amounts of the inhibitor can be supplied. Since the amino-acid sequence of the porcine complement inhibitor can be determined from the base sequence of pMCPcDNA and the DNA coding the porcine complement inhibitor can be synthesized from the amino-acid sequence, the porcine complement inhibitor can also be produced by genetic engineering with such DNA. By genetic engineering, not only the protein consisting of a naturally-existing sequence but also those with one or more amino-acid replaces, inserts, or deletions and those conjugated with other proteins can be produced. Moreover, pMCPcDNA of this invention is useful for analysis of the porcine complement-inhibitor promoter region.

Complement-inhibitor cDNA of various animal species can easily be obtained by the screening method of this invention.

EXAMPLES

The present invention will be specifically explained in detail with actual examples, but the scope of the invention is not restricted to these samples.

Example 1

1) Extraction of Total RNA From Porcine Vascular Endothelial Cells and Purification of Poly(A)⁺RNA

Primary culture cells of porcine vascular endothela or PAE cells (1×10⁸ cells) were placed in 15-cm dishes and then 3 ml of a 5.5 M GTC (guanidine thiocyanate) solution was added to each dish. At this step, the mixture was viscous due to a high DNA content, so suction and discharge of the mixture were repeated 20 to 30 times with a 30-ml syringe with a 18-gauze needle to decrease the viscosity.

Then, after centrifugation (800 rpm), the sediment was discarded. The supernatant was overlaid on top of a CsTFA solution (17 ml) in a polyallomer (propylene-ethylene block copolymers) tube (40 ml) and ultracentrifuged overnight. The upper GTC and intermediate DNA phases were carefully taken; the rest was discarded. The tube was inverted upside down to remove excess water. A 2-cm portion from the bottom was cut off and placed on ice. RNA in the tube bottom was scraped with an edge of a micro-pipette tip and dissolved in 600 μl of a 4 M GTC solution. Insoluble substances were sedimented by light centrifugation. To the 600-μl solution, 15 μl of 1 M acetic acid and 450 μml of ethanol were added. The solution was chilled for longer than 3 h at −20° C. and then centrifuged for 10 min in a microtube (4° C.).

After removing the supernatant, RNA was immediately dissolved in 1 ml of freshly prepared TE buffer (10 mM Tris-HCl and 1 mM EDTA, pH 8.0). After light centrifugation, the supernatant was taken. After addition of 13 μl of 2 M NaCl per 330 μl of the supernatant and then chilling for longer than a few hours at −20° C., the total RNA was prepared.

Poly (A)⁺RNA was isolated and purified from the total RNA by an mRNA purification kit commercially available from Clontech (in principal, affinity chromatography on an oligo (dT) cellulose column). Namely, after washing several times a dT resin-packed column with a washing buffer, a sample was loaded on the column, which was washed again with the washing buffer. The RNA (mRNA) absorbed onto the dT resin was eluted with an elution buffer, sedimented with ethanol, and then subjected to cDNA preparation.

2) Preparation of a cDNA Library

The mRNA (4 μg) obtained was filled up to 17 μl with distilled water, which was heated for 5 min at 68° C. After 10-min chilling on ice, the following were added:

| | |
|---|---|
| ×5 First strand buffer | 6 μl |
| 0.1M DTT | 3 μl |
| RNasin | 1 μl |
| Linker primer (1.6 μg/μl) | 3.3 μl |
| dNTP solution (10 mM) | 2 μl |

The mixture was stirred immediately after addition of them and allowed to stand for 2 min at 43° C. Super script 11 was added to it, incubated for an hour at 43° C., and then placed on ice.

Then, the following were added to the mixture on ice:

| | |
|---|---|
| ddH₂O | 134.3 μl |
| ×5 Second strand buffer | 48 μl |
| dNTP solution (10 mM) | 4 μl |
| 0.1M DTT | 9 μl |

After allowing to stand for 5 min on ice, the following were added:

| | |
|---|---|
| DNA polymerase (5 U/μl) | 12 μl |
| Rnase H (1.5 U/μl) | 2.7 μl |

Immediately thereafter, the mixture was stirred, incubated for 150 min at 16° C., and 4 μl of T4 DNA polymerase (3 U/μl) was added. It was then incubated for 15 min at 16° C. and then for 10 min at 37° C., and extracted with 250 μl of phenol/chloroform and with the same extractant containing 100 μl of TE. The extracts were pooled., to which the following were added:

| | |
|---|---|
| 3M sodium acetate | 40 μl |
| Carrier (glycogen) | 10 μl |
| 100% ethanol | 1 ml |

The mixture was incubated overnight at −20° C. (or for an hour at −80° C.), centrifuged (for 20 min at 15,000 rpm), and then washed with 70% ethanol. After centrifugation (for 5 min at 15,000 rpm), the sediment was dissolved in 15 μl of TE.

To the solution obtained (4 μl), the following were added on ice:

| | |
|---|---|
| 10× Ligation buffer | 2 μl |
| Sal I adapter (1 μg/μl) | 1.2 μl |
| ddH₂O | 9.8 μl |
| T4 DNA ligase | 10 units (approximately 3 μl) |

The mixture was incubated overnight at 8° C. and then inactivated by heating for 30 min at 70° C. Then, the following were added to the solution (20 μl):

| | |
|---|---|
| Not I buffer (Toyobo H) | 6 μl |
| ×10 Triton | 4 μl |
| ×100 BSA | 0.4 μl |
| ddH₂O | 5.6 μl |
| Not I (500 U/μl) | 4 μl |

The mixture was incubated for 2 h at 37° C. and then inactivated by heating for 30 min at 70° C. The following were added to the solution:

| | |
|---|---|
| 1M NaCl | 7 μl |
| ddH₂O | 22 μl |
| Glycogen (10 μg/μl) | 1 μl |

The mixture was loaded on a small-scale centrifuging gel-filtration apparatus (for 3 min at 3,000 rpm), desalted with a Millipore filter (UFCP3 TK50), and then centrifuged (for 5 min at 10,000 rpm). After removing the supernatant, 100 μl of TE was added to the sediment,which was centrifuged (for 15 min at 10,000) at −80° C. After removal of the supernatant, and 100 μl of TE was added to the sediment, which was centrifuged (for 15 min at 10,000 rpm). After removal of the supernatant, 100 μl of TE (1/10) was added to the sediment, which was centrifuged (for 20 min at 10,000 rpm). After removal of the supernatant, the sediment was suspended in 30 μl of TE (1/10). cDNA was obtained by centrifugation (twice each for 5 s at 5,000 rpm) by placing the filter upside down.

Then, the following were admixed on ice:

| | |
|---|---|
| cDNA | 30 μl |
| Expression vector [pMSF + (HygroB)] | 21 μl |
| ×10 Ligation buffer | 12 μl |
| ddH$_2$O | 56 μl |
| T4 DNA ligase (4.6 U/μl) | 1.5 μl |

After mixing, the mixture was allowed to stand overnight at 8° C., heated for 30 min at 70° C., and desalted with a Millipore filter (UFCP3 TK50). It was centrifuged (for 15 min at 10,000 rpm), and again (for 15 min at 10,000 rpm) after addition of 100 μl of TE. After removal of the supernatant, 100 μl of TE was added to the sediment, which was centrifuged (for 15 min at 10,000 rpm). After removal of the supernatant, 100 μl of TE (1/10) was added to the sediment, which was centrifuged. After removing the supernatant, sediment was dispersing in 30 μl of TE (1/10). This was centrifuged (for 5 s at 5,000 rpm) by placing the filter upside down, and 30 μl of a cDNA library (1.2×10$^6$ clones, mean size: 1.5 kbp) was obtained. Outline of the structure of cDNA obtained is illustrated in FIG. 1.

3) Cloning pMCPcDNA

Human lymphoblast JY25 cells at a logarithmic phase (1×10$^8$/10 cuvettes) were suspended in HeBS (800 μl), to which the above-described cDNA library (20 μl/10 cuvettes) was added. The mixture was electroporated (250V, 960 μF).

The electroporated cells were suspended in 200 ml of DMEM [containing 20% FCS, IT (insulin/transferrin), and PS (penicillin/streptomycin)] and incubated for 24 h. The cells were resuspended in DMEM (containing 10% FCF, IT and PS) supplemented with hygromycin B in 400 μg/ml, incubated for 10 to 14 days (1×10$^7$ cells) and then washed with PBS.

The washed cells were subjected to complement selection. Namely, DMEM for selection (containing 10 ml of FCS+10 ml of porcine complement+80 ml of DMEM+1 ml of anti-JY25 antibody+667 μg of anti-DAF antibody+100 μg of anti-MCP antibody) was added to the cells, which were incubated for 2 h at 37° C. After the reaction, the surviving cells were washed once with DMEM and counted by the Trypan-blue-staining method (the surviving cells: 0.1 to 1%). The anti-DAF and anti-MCP antibodies were added to improve the selectivility. The surviving cells were washed with PBS, suspended in 100 ml of DMEM (10% FCS) and then incubated for 24 h.

Then, culture in the hygromycin-B-containing medium and the complement selection were repeated twice (the final surviving cells became 20%).

The surviving cells (1×10$^6$ obtained were centrifuged (for 5 min at 1,000 rpm), washed with PBS, mixed well with 400 μl of a 0.6% SDS/10 mM EDTA mixture, and then allowed to stand for 20 min at room temperature. After addition of 100 μl of 5 M NaCl and mixing well (the cells discolored to white), the suspension was allowed to stand overnight at 4° C. and then centrifuged (for 15 min at 15,000 rpm) to obtain the supernatant. To the supernatant, phenol/chloroform (200+200 μl) was added. After centrifugation (for 2 to 3 min at 12,000 rpm), the supernatant was taken. The supernatant, to which 10 μl (4 μg) of polyacrylamide and then 1 ml of ethanol were added, was allowed to stand for 2 h at −80° C. After addition of 70% ethanol and washing, the sediment was suspended in 20 μl of TE.

cDNA (2 μl) thus obtained was electroporated (2.5 kV, 25 μF, 400 Ω) into 50 μl of *Escherichia coli* (MC1061). Immediately thereafter, 950 μl of SOC medium was added to the sample in each cuvette (total 10 cuvettes), which was incubated for an hour at 37° C. with stirring (20 rpm). The incubated samples were treated in the following way:

(1) The sample (15 μl/plate) was smeared on plates, which were stored at 4° C.

(2) The remaining sample was added to 2 ml of TBK+, which was incubated overnight at 37° C. with stirring, and subjected to purification in miniature scale (small-scale preparation of plasmid DNA). cDNA purified in miniature scale (2 ml of the sample) was suspended in 20 μl of TE. Of cDNA obtained, a 10-μl portion was digested with restriction enzymes (Xho I+Not I) and electrophoresed in agarose gel to examine for the cDNA size. The remaining sample was electroporated into JY25 cells, which were selected by the complement-selection method described earlier and subjected to viable count.

Figure 2:
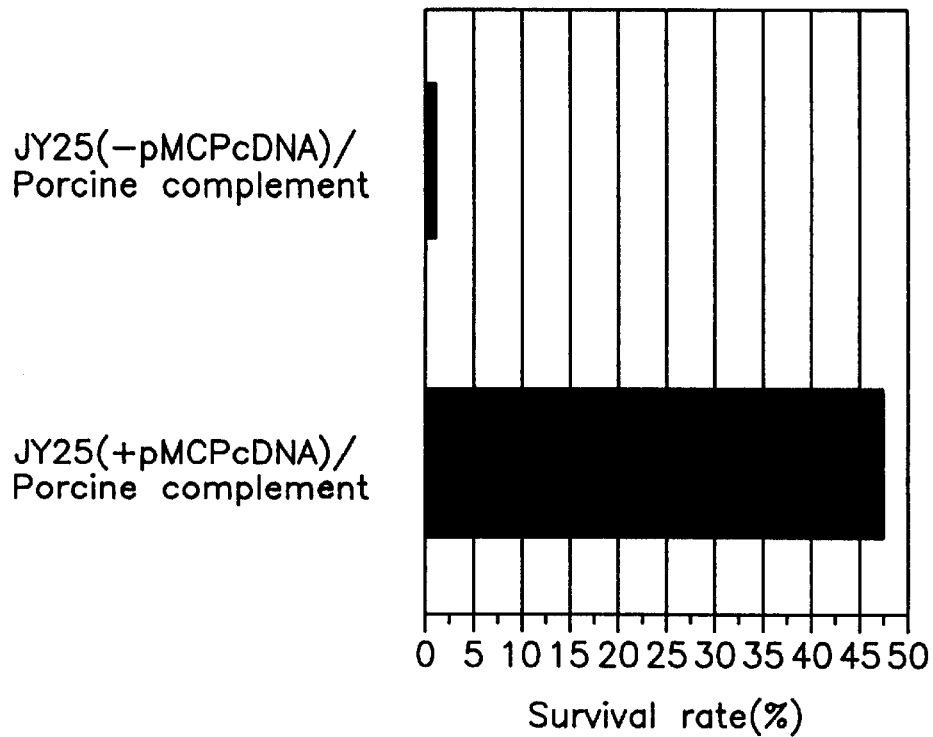
FIG. 2 shows survival rates of JY25 cells transformed with the porcine complement-inhibitor cDNA (pMCPcDNA) of this invention and determined by the complement-selection method.

After the above-described check, 40 colonies were fished from the plates with the highest surviving rate and incubated overnight in 2 ml of TKB+. The culture was purified in miniature scale and digested with the restriction enzymes (Xho I+Not I). After checking the size of cDNA inserted, clones were classified according to the cDNA size. cDNA having a proper size and insertion frequency and bulk DNA (control) were each electroporated again into JY25 cells and analyzed by the complement-selection method. The results are shown in FIG. 2, which tells that the cells introduced with the bulk cDNA [JY25(−pMCPcDNA)] showed a very low survival rate, whereas those with the selected cDNA (pMCPcDNA) [JY25(+pMCPcDNA)] showed a very high survival rate and resistance against the porcine complement.

cDNA was isolated from the cells showing a high survival rate, digested with the restriction enzymes (Xho I+Not I), conjugated to pBSIIKS+ and sequenced by a conventional method. The result showed that the cDNA comprised a 1,365-bp base sequence (Sequence No. 1) and that the coding region of the porcine complement inhibitor was 1,089 bp, of which an approximately 600-bp translation region was highly homologous (approximately 70%) to human MCPcDNA. The amino-acid sequence of the porcine complement inhibitor from the base sequence of Sequence No.1 is shown in Sequence No. 2. The number of total amino-acid residues were 363.

What is claimed is:

1. DNA comprising the base sequence comprising SEQ ID NO:1 or a fragment thereof.

2. DNA comprising the 59$^{th}$-to-1,147$^{th}$ bases of the base sequence comprising SEQ ID NO:1.

3. A porcine complement inhibitor comprising the amino-acid sequence comprising SEQ ID NO:2.

4. DNA encoding the amino-acid sequence comprising SEQ ID NO:2.

5. A method comprising
   introducing a cDNA library comprising DNA encoding the amino acid sequence of SEQ ID NO:2 to host cells;
   adding anti-host antibodies and complement components and;
   selecting surviving host cells to screen for clones containing a complement-inhibitor gene.

6. A method comprising introducing a porcine cDNA library into host cells;
   adding anti-host antibodies and complement components in the presence of anti-host complement inhibitor antibodies; and
   selecting surviving host cells to screen for clones containing a complement inhibitor gene.

* * * * *